(12) United States Patent
Blanco Barrio et al.

(10) Patent No.: US 8,507,188 B2
(45) Date of Patent: Aug. 13, 2013

(54) FLEXIBLE MICRO/NANOFLUIDIC DEVICES (75) Inventors: Francisco Javier Blanco Barrio, Mondragón (ES); Maria Aguirregabiria Izaguirre, Mondragón (ES); Aitor Ezkerra Fernandez, Mondragón (ES); Janette Lilian Maria Schulze, Mondragón (ES); Jesús Miguel Ruano Lopez, Mondragón (ES); Kepa Mayora Oria, Mondragón (ES)

(73) Assignee: Poc Microsolutions, S.L., Arrasate (ES)

( * ) Notice: Subject to any disclaimer, the term of this patent is extended or adjusted under 35 U.S.C. 154(b) by 608 days.

(21) Appl. No.: 12/301,967

(22) PCT Filed: May 22, 2007

(86) PCT No.: PCT/ES2007/000296
§ 371 (c)(1),
(2), (4) Date: Aug. 10, 2010

(87) PCT Pub. No.: WO2007/135214
PCT Pub. Date: Nov. 29, 2007

(65) Prior Publication Data
US 2010/0304306 A1 Dec. 2, 2010

(30) Foreign Application Priority Data
May 22, 2006 (ES) ............... P200601322

(51) Int. Cl.
*G03F 7/20* (2006.01)

(52) U.S. Cl.
USPC .......................... 430/320; 430/330

(58) Field of Classification Search
USPC .................................. 430/319, 320, 330
See application file for complete search history.

(56) References Cited

U.S. PATENT DOCUMENTS

| | | | |
|---|---|---|---|
| 4,882,245 A | 11/1989 | Gelorme et al. | |
| 6,844,213 B2 | 1/2005 | Sparks | |

OTHER PUBLICATIONS

Abgrall et al. "A novel fabrication method of flexible and monolithic 3D microfluidic structures using lamination of SU-8 films." *J. of Micromechanics and Microeng.* vol. 16. 2006. pp. 113-121.
Agirregabiria et al. "Fabrication of SU-8 multilayer microstructures based on successive CMOS compatible adhesive bonding and releasing steps." *Lab Chip.* vol. 5. 2005. pp. 545-552.
Arscott et al. "A planar on-chip micro-nip interface for NanoESI-MS microfluidic applications." *J. Micromec. Microeng.* vol. 14. 2004. pp. 310-316.
Becker et al. "Polymer microfluidic devices." *Talanta.* vol. 56. 2002. pp. 267-287.
Blanco et al. "Novel three-dimensional embedded SU-8 microchannels fabricated using a low temperature full wafer adhesive bonding." *J. Micromech. Microeng.* vol. 14. 2004. pp. 1047-1056.
Despont et al. "High-Aspect-Ratio, Ultrathick, negative-tone near-uv photoresist for MEMS applications." *IEEE.* 1997. pp. 518-522.

(Continued)

*Primary Examiner* — Brittany Raymond
(74) *Attorney, Agent, or Firm* — Merchant & Gould P.C.

(57) ABSTRACT

The present invention relates to a method for manufacturing micro/nanofluidic devices that incorporate overhanging micromechanical and metal components monolithically integrated with the fluidic circuitry.

16 Claims, 7 Drawing Sheets

(56) References Cited

OTHER PUBLICATIONS

Lee et al. "Biocompatible benzocyclobutene-based intracortical neural implant with surface modification." *J. Micromech. Microeng.* vol. 15. 2005. pp. 2149-2155.

Lee et al. "Polyimide-based intracortical neural implant with improved structural stiffness." *J. Micromech. Micreng.* vol. 14. 2004. pp. 32-37.

Metz et al. "Polyimide-based microfluidic devices." *Lab on a Chip.* vol. 1. 2001. pp. 29-34.

Papageorgiou et al. "A Shuttered probe with in-line flowmeters for chronic in-vivo drug delivery." *IEEE.* 2001. pp. 212-215.

Razzacki et al. "Integrated microsystems for controlled drug delivery." *Adv. Drug Delivery Reviews.* vol. 56. 2004. pp. 185-198.

Reyes et al. "Micro Total Analysis Systems. 1. Introduction, Theory, and Technology." *Anal. Chem.* vol. 74. 2002. pp. 2623-2636.

Schmitt-Kopplin et al. "Capillary electrophoresis—mass spectrometry: 15 years of developments and applications." *Electrophoresis.* vol. 24. 2003. pp. 3837-3867.

Takeuchi et al. "Parylene flexible neural probes integrated with microfluidic channels." *Lab Chip.* vol. 5. 2005. pp. 519-523.

Tuomikoski et al. "Free-standing SU-8 microfluidic chips by adhesive bonding and release etching." *Sensors and Actuators.* vol. 120. 2005. pp. 408-415.

Voskerician et al. "Biocompatibility and biofouling of MEMS drug delivery devices." *Biomaterials.* vol. 24. 2003. pp. 1959-1967.

Tuomikoski et al. "Free-standing SU-8 microfluidi chips by adhesive bonding and release etching." *Sensors and Actuators.* vol. 120. 2005. pp. 408-415.

Ruano-Lopez et al. "A new SU-8 process to integrate buried waveguides and sealed microchannels for Lab-on-Chip." *Sensors and Actuators.* vol. 114. 2006. pp. 542-551.

Blanco et al. "Novel three-dimensional embedded SU-8 microchannels fabricated using a low temperature full wafer adhesive bonding." *Journal of Micromechanics and Microengineering.* vol. 14. 2004. pp. 1047-1056.

Agirregabiria et al. "Fabrication of SU-8 multilayer microstructures based on successive CMOS compatible adhesive bonding and releasing steps." *Lap Chip.* vol. 5. 2005. pp. 545-552.

Multiple microfluidic channels

FLEXIBLE MICRO/NANOFLUIDIC DEVICES

This application is a National Stage Application of PCT/ES2007/000296, filed 22 May 2007, which claims benefit of Serial No. P200601322, filed 22 May 2006 in Spain and which application(s) are incorporated herein by reference. To the extent appropriate, a claim of priority is made to each of the above disclosed applications.

FIELD OF THE INVENTION

The present invention is generally comprised within the field of flexible polymeric devices and specifically within the field of polymeric micro/nanofluidic devices integrated with flexible electronic and micromechanical components.

STATE OF THE ART

The first microfluidic structures were developed at the start of the 1990s (Darwin R. Reyes, Dimitri Iossifidis, Pierre-Alain Auroux and Andreas Manz. Micro Total Analysis Systems. 1. Introduction, Theory, and Technology. Anal. Chem. 2002, 74, 2623-2636). These structures were manufactured using materials such as silicon and glass due to the fact that the techniques for micromanufacturing on these substrates were developed by the microelectronics industry. The field of application of these devices with the best prospects is in new biochemical analysis applications and the highly accurate delivery of different types of drugs. Disposable single-use devices are necessary for most of these applications. Silicon and glass are expensive materials for these types of applications, which require larger devices than microelectronic devices, due to both the cost of the material and the cost associated to the manufacturing processes, especially slow and expensive in the case of glass. For this reason, techniques for manufacturing in polymers with microchannels, such as the microreplication (hot embossing) process, the microinjection and the micromachining thereof, have been developed in the last few years. New sealing processes for sealing microchannels in polymers such as lamination and melt-sealing, a critical step in the manufacture of these devices have also been developed (Holger Becker, Laurie E. Locascio "Polymer microfluidic devices" Talanta 56 (2002) 267-287). Furthermore, most polymers have a higher level of biocompatibility than silicon and glass (Gabriela Voskerician et al. Biocompatibility and biofouling of MEMS drug delivery devices. Biomaterials 24 (2003) 1959-1967).

During the last few years, certain applications such as the drug delivery [S. Zafar Razzacki. Integrated microsystems for controlled drug delivery. Advanced Drug Delivery Reviews 56 (2004) 185-198] or electrospray ionization for applications in mass spectroscopy (Philippe Schmitt-Kopplin. Capillary electrophoresis-mass spectrometry: 15 years of developments and applications. Electrophoresis 2003, 24, 3837-3867) (Steve Arscott et al. A planar on-chip micro-nib interface for NanoESI-MS microfluidic applications. J. Micromech. Microeng. 14 (2004) 310-316) have created the need to develop microfluidic structures with a very small thickness (between 50 to 250 microns) that in many cases are flexible and have a high resolution. In some cases, these devices must have resolutions in nanometric dimensions.

Microfluidic structures manufactured in substrates with a thickness between 50-250 microns have recently been manufactured, using silicon substrates with a thickness of 500 microns (Sparks U.S. Pat. No. 6,844,213 B2 Jan. 18, 2005). Silicon is photolithographed and etched by means of classic microelectronic manufacturing techniques, until creating structures with small thicknesses that incorporate microfluidic channels and metal electrodes therein. Other similar developments have included micromechanical fluidic control elements manufactured in silicon (D. Papageorgiou. A shuttered probe with in-line flowmeters for chronic in vivo drug delivery. Proceedings of IEEE MEMS 2001. 212-215)

As has been mentioned above, for many of these applications, silicon is not a suitable material due to the cost of the material and its level of biocompatibility as well as to the extreme brittleness of such thin silicon structures. During the last few years, the new technologies on polymeric materials have been modified to obtained thinner structures and with a higher degree of flexibility. Technologies have thus been developed on materials such as Polymides (PI) [S. Metz et al. Polymide-based microfluidic devices. Lab Chip, 2001, 1, 29-34], Benzocyclobutene (BCB) 1 (Keekeun Lee et al. Biocompatible benzocyclobutene-based intracoridal neural implant with surface modification. J. Micromech. Microeng. 15 (2005) 2149-2155), Parileno (Shoji Takeuchi, D. Zielgler, Y Yoshida, K. Mabuchi and T. Suzuki. Lab Chip, 2005, 5, 519-523) and SU-8 (Patrick Abgrall et al. A novel fabrication method of flexible and monolithic 3D microfluidic structures using lamination of SU-8 films. J. Micromech. Microeng. 16 (2006) 113-121) (Santeri Tuomikoski. Free-standing SU-8 microfluidic chips by adhesive bonding and release etching. Sensors and Actuators A 120 (2005) 408-415).

The techniques for manufacturing these microfluidic structures in polymers are based on creating microfluidic channels by means of different techniques, such as those of planar microelectronic manufacture (photolithography, depositing of thin sheets and wet and dry etching), micromachining by laser or microreplication on the polymeric material. The microfluidic channels are sealed and encapsulated using specific sealing techniques such as melt-sealing (bonding) or microlamination. These flexible polymeric microfluidic devices must be transported in a rigid support for the manufacture thereof. They must be deposited and process on these rigid substrates (mainly silicon). Once the manufacture of the polymeric structures has ended, they are released from the substrates on which they have been processed.

In the case of microfluidic devices created in BCB and PI, the devices developed must receive special treatments to provide these structures with greater rigidity, due to the excessive flexibility of these materials in such small thicknesses (Keekeun Lee. Biocompatible benzocyclobutene-based intracortical neural implant with surface modification. J. Micromech. Microeng. 15. 2005. 2149-2155) (Kee-Keun Lee. Polymide-based intracortical neural implant with improved structural stiffness. J. Micromech. Microeng. 15. 2004. 32-37). In these works, one of the rigid substrates (silicon) supporting the structures during the manufacture has been maintained. This substrate is etched by means of dry plasma etching techniques, to leave a thin layer of silicon of about 20 microns, below polymeric structures. The device thus has greater rigidity. This solution is slow and expensive, increasing the cost of the materials used and the associated manufacturing process.

During the last few years, new microfluidic technologies have been developed using the thermosetting polymer SU-8 (U.S. Pat. No. 4,882,245, Nov. 21, 1989). SU-8 is a material having good biocompatibility (Gabriela Voskerician et al. Biocompatibility and biofouling of MEMS drug delivery devices. Biomaterials 24 (2003) 1959-1967). Furthermore, it is one of the most suitable materials for applications in the microfluidics field given its high versatility when manufacturing microfluidic channels of different sized and due to its excellent chemical, optical and mechanical properties [Despont M, Lorennz H, Fahrni N, Brugger J, Renaud P and Vetiger P 1996 High aspect ratio, ultrathick, negative-tone near-UV photoresist for MEMS applications Proc. IEEE'96 (San Diego, Calif., January 1996) pp 162-7]. It is important to emphasize that the manufacture of the SU-8 polymer is compatible with the lines for manufacturing microelectronic integrated circuits (CMOS), which opens up the possibility of their mass production.

SU-8 has been used in the last few years in many microfluidic applications, among which those of miniaturized electrophoresis devices (M. Aguirregabira et al. Sodium dodecyl sulfate-capillary gel electrophoresis of proteins in microchannels made of SU-8 films. In preparation for the Electrophoresis journal) or of electrospray ionization (Steve Arscott et al. A planar on-chip micro-nib interface for NanoESI-MS microfluidic applications. J. Micromech. Microeng. 14 (2004) 310-316) must be emphasized. Given the fact that SU-8 does not need treatments to improve its rigidity, and that it is flexible enough for many of the mentioned applications, it is one of the materials with the best prospects for the development of commercial devices.

New techniques have been developed for manufacturing free and flexible microfluidic devices based on SU-8 (Patrick Abgrall et al. A novel fabrication method of flexible and monolithic 3D microfluidic structures using lamination SU-8 films. Journal of Micromechanc. and Microeng. 16 1113-121) (Santeri Tuomikoski et al Free-standing SU-8 microfluidic chips by adhesive bonding and release etching. Sensors and Actuators A 120. 2005. 408-415). In these manufacturing technologies, non-polymerized layers of SU-8 have been used for sealing the microfluidic channels, a critical step in the manufacturing process of this material. Due to this, the polymerization and developing process necessary for obtaining microfluidic devices is carried out once the sealing of the channels has ended. This can cause a considerable contamination of the devices during the curing and developing process. In the case of the development of Patrick Abgrall et al, the microfluidic channels cannot have sealing covers greater than 50 microns, which limits the use pressures of the devices. In addition, due to the viscous (non-polymerized) state of the material during the sealing process (which is carried out applying pressure and temperature), the possibility of the microchannels collapsing and being deformed due to the flow of the polymer in viscous state is very high. This makes it difficult to design the microfluidic channels and worsens the definition thereof. The structures are seriously limited in thickness and distance between adjacent channels. In the process developed by Santeri Tuomikoski et al, the process for releasing the SU-8 structures in the rigid substrate must be carried out with aggressive chemical etching agent such as hydrofluoric acid. The work mentions that said chemical etching agents can etch the structures which have been previously formed, reducing the quality thereof.

It is important to emphasize that none of the mentioned polymeric technologies has incorporated micromechanical control elements in their manufacturing processes.

There is therefore a need to develop polymeric microfluidic devices the resolution and definition of which is not limited by their manufacturing process, nor is there the possibility of contamination during the manufacture, which do not give bioincompatibility reactions and that the manufacturing process has a low cost.

DESCRIPTION OF THE INVENTION

The present invention relates to a method for manufacturing micro/nanofluidic devices that incorporate overhanging micromechanical and metal components monolithically integrated with the fluidic circuitry, by means of the sealing of previously polymerized and structured layers. These layers are subsequently released from the substrate without the need for chemical etching, said manufacturing method further allows manually cutting the devices, such that it solves the problems existing in the state of the art.

Thus, a first aspect of the present invention relates to a method for manufacturing micro/nanofluidic devices comprising:
  a) depositing a thermosetting polymeric photoresin (3) on two substrates of polymeric material (2) covering the surface of two independent substrates (wafer 1) and (wafer 1').
  b) photolithographing at low temperature the layers of thermosetting polymeric photoresin (3) deposited in step a)
  c) depositing the metal type components in at least one wafer
  d) microstructuring the metal components deposited in step c)
  e) depositing a layer of thermosetting polymeric photoresin (3) on wafer 1'
  f) photolithographing and developing at low temperature the thermosetting polymeric photoresin deposited on wafer 1'
  g) sealing at low temperature the wafers 1 and 1' obtained by means of superimposing them with the surfaces of the photoresin facing one another
  h) releasing the micro/nanofluidic structures from the substrates of biocompatible polymeric material
  i) cutting the devices In a particular embodiment of the present invention, the thermosetting polymeric photoresin is preferably an epoxy resin. In a more particular embodiment, the thermosetting polymeric photoresin is SU-8.

When the present invention refers to SU-8, reference is made to a polymeric resin with an epoxy base, reference is specifically made to a chloromethyloxirane formaldehyde 4,4'-(1-methylethylidene)bis-phenol polymer.

In a particular embodiment of the present invention, the thermosetting polymeric photoresin is deposited on the rigid and independent substrates of biocompatible polymeric material by means of spinning depositing techniques.

In a particular embodiment of the present invention, step a) of depositing the thermosetting polymeric photoresin on the two rigid and independent substrates of biocompatible polymeric material covering the surface of the wafers 1 and 1' is repeated at least once to reach a greater thickness of the layer of photoresin. In a more particular embodiment of the present invention, the thickness of the deposited layer of thermosetting polymeric photoresin is 20 and 35 microns.

In a particular embodiment of the present invention, the rigid and independent substrates of biocompatible polymeric material can be, for example: methacrylate (PMMA), zeonex, zeonor, kapton, PI, PET, mylar, or any polymeric material known by a person skilled in the art having low adherence with the thermosetting photoresin.

In a particular embodiment of the present invention, the photolithography at low temperature of step b) and/or of step f) is carried out at temperatures below the glass transition temperature of the polymer, the temperature at which the photolithography is carried out is preferably comprised between 80-95° C. In a particular embodiment, the photolithography at low temperature is carried out by means of illumination, more particularly the illumination is with ultraviolet light.

In a particular embodiment of the present invention, the photolithography at low temperature carried out in wafer 1 is carried out by means of applying discontinuous illumination on the surface of the thermosetting polymeric photoresin.

In a particular embodiment of the present invention, the photolithography at low temperature carried out in wafer 1' is carried out by means of applying continuous illumination on the entire surface of the thermosetting polymeric photoresin.

In a particular embodiment of the present invention, after the photolithography of step b), the metal components (4) are deposited on the thermosetting polymeric photoresin (3) and substrate of polymeric material (2) covering the surface of wafer 1'.

When the present invention refers to metal components, reference is made to conductive metal components, such as for example, gold, chromium, aluminium, titanium, and/or ferromagnetic components such as for example nickel, cobalt, etc.

When the present invention refers to the microstructuring of the metal components, reference is made to microstructuring techniques known by a person skilled in the art such as for example, cathode sputtering, wet and dry etching, electrodeposition.

In a particular embodiment of the present invention, step e) of depositing the layer of thermosetting polymeric photoresin on wafer 1' is repeated at least once.

In a particular embodiment of the present invention, there is a step prior to step g), in which overhanging micromechanical structures are made.

In the context of the present invention, the term "overhanging micromechanical structures" relates to elements suspended by means of at least one anchoring and with at least one degree of freedom of movement.

In a particular embodiment of the present invention, the sealing at low temperature of wafers 1 and 1' is carried out at temperatures below the glass transition temperature of the polymer, the temperature at which the photolithography is carried out is preferably comprised between 80-120° C.

In a particular embodiment of the present invention, the micro/nanofluidic structures of step h) are released by means of ultrasound in an alcohol bath.

In a particular embodiment of the present invention, the micro/nanofluidic devices of step i) are cut manually.

In the context of the present invention, the term "micro/nanofluidic devices" relates to devices containing microchannels (6) with dimensions comprised between 500 microns and 500 nanometers, such as for example, microcannulas, devices for clinical diagnosis, micromixers, electrophoresis chips, electrospray chips, etc.

A second aspect of the present invention relates to a micro/nanofluidic device obtained by a previously described method and comprising at least one micro/nanofluidic channel. In a particular embodiment, the thickness dimensions of the device are comprised between 500 microns and 500 nanometers. In a particular embodiment, the micro/nanofluidic channels comprise dimensions between 5 and 500 microns in width and between 1 and 500 microns in height. In a particular embodiment the micro/nanofluidic channels comprise between 10 and 200 microns in height.

In a particular embodiment, the micro/nanofluidic device can comprise microchambers with dimensions comprised between 1 and 5 mm in width and between 20 and 180 microns in height.

In a particular embodiment of the present invention, the micro/nanofluidic device comprises metal type components, in a particular embodiment the metal type components are conductive metals or ferromagnetic metals.

In a particular embodiment, the metallic type components are microelectronic components such as for example sensors, electrodes.

A third aspect of the present invention relates to the use of a previously described micro/nanofluidic device for clinical diagnosis, medicinal product delivery, fluid extraction, neural prostheses, electrophoresis chips, microcannulas, microprobes.

DETAILED DESCRIPTION OF AN EMBODIMENT

The method of the present invention is based on the use of photolithography and sealing techniques at temperatures below 100° C. (F J Blanco et al. Novel three dimensional embedded SU-8 microchannels fabricated using a low temperature full wafer adhesive bonding. Journal of Micromechanics and Microengineering 14 (2004) 1047-1056) (M. Agirregabiria the al. Fabrication of SU-8 multilayer microstructures based on successive CMOS compatible adhesive bonding and releasing steps Lab chip 2005, 5, 545-552) of thermosetting polymeric photoresins (SU-8) (U.S. Pat. No. 4,882,245, Nov. 21, 1989) which allow manufacturing very high resolution (from between 500 nanometers to 500 microns in width, and from 1 to 200 microns in height) microfluidic structures on two rigid substrates on which a plastic material on which SU-8 has low adherence, for example a Polymide (Kapton), PET or Mylar, has been reversibly deposited, adhered or laminated. These polymeric materials have a low adhesion to SU-8 therefore they allow, once the process has ended, completely releasing the structures from the substrate on which they have been manufactured. Furthermore, manufacturing processes for monolithically integrating overhanging micromechanical components and integrated metal lines have been developed in the present invention.

The different manufacturing steps, optimization of the bonding process for forming the microchannels and the fluidic characterization thereof are described below.

The manufacturing process of the invention began with depositing the SU-8 photoresin (3) by means of spinning techniques in two transparent rigid wafers (1 and 1'), which can be made of different material such as for example of glass, methacrylate or COC polymers, on which a layer of biocompatible polymeric material (2) such as for example Kapton, PI or PET (FIG. 1) has been deposited, adhered or laminated. In this example, Kapton with a minimum thickness of 250 microns was used as the substrate of biocompatible polymeric material, which provided enough rigidity for the subsequent depositing and photolithography steps. The spinning process was carried out on a rotating plate which allowed uniformly spinning the SU-8. The SU-8 was deposited on the substrates and then the plate was rotated. The thickness of the deposited layer, which can be 1-500 microns thick, depends on the speed and time of rotation of the plate. In this particular example, layers with a thickness of 20 microns were obtained, and therefore the process was carried out in two steps, a first step for 5 second at 600 revolutions per minute (r.p.m.) with an acceleration of 200 r.p.m./second and a second step of 5000 r.p.m. and with an acceleration of 600 r.p.m./second for 60 seconds. In other particular examples, layers with a greater thickness (35 microns) were deposited in order to increase the height of the microchambers or microchannels, to that end they were carried out in two steps, a first step for 5 seconds at 600 revolutions per minute (r.p.m.) with an acceleration of 200 r.p.m./second and a second step of 3000 r.p.m. and with an acceleration of 600 r.p.m./second for 60 seconds. To achieve the desired thickness, the process was repeated several times with layers with different thicknesses. As a result, the SU-8 was uniformly deposited over the entire substrate, forming different layers, with a thickness determined by the spinning process, if only one layer has been spun, or by different layers deposited on top of one another. These layers were then subjected to a thermal process (soft bake) at a temperature between 75° C. and 100° C. for 7 minutes in the case of films of 20 microns, and 10 minutes for films with thicknesses up to 100 microns, in a flat hot plate. For films with thicknesses greater than 100 microns, a thermal treatment of more than 12 minutes is carried out. The temperature of the plate was increased to temperatures between 75 and 100° C. The solvent residues that were not eliminated during the depositing evaporated in this process and the deposited resin became uniform. Once the thermal process had finished, the deposited polymer was microstructured using standard photolithography techniques.

The photolithographic structuring process began with an ultraviolet illumination process in a contact aligner (standard Suss MA6 photolithography equipment). Only the areas giving rise to the microstructures (microchannels (6)) once the process had ended were exposed to ultraviolet light through a mask placed in the aligner. The ultraviolet dose that was used for photolithographies of layers of 20 microns was 140 mJ/cm$^2$. For two successively deposited layers with a thickness of 20 and 35 microns (total layer of 55 microns) the dose was 200 mJ/cm$^2$. Then a thermal treatment was performed which hardened (polymerized) the SU-8 of the exposed areas at a temperature between 80 and 95° C. for 3 minutes for layers of 20 microns, and 4 minutes for layers of 55 microns. Once hardened, the non-exposed areas were chemically developed such that the microchannels (6) were defined on the SU-8. This development was performed with the standard SU-8 photoresin developer (propylene glycol monomethyl ether acetate, PGMA). The non-exposed parts were eliminated during development, leaving the microstructures on the substrate. Once the manufacturing process had ended, these structures were established as the guides for the microchannels. Due to the nature of the photolithographic process, these microchannels were aligned in the PMMA wafers without any problems with substrate deformation and with a 1 micron resolution, the photolithographic mask aligner (Suss MA6) resolution.

In one of these layers, channels were not made and a metal layer (4) which was later structured was deposited. The metal layer can be made of different materials (gold, platinum, silver, chromium, titanium, etc, or combinations thereof), in this particular case gold and chromium were deposited. The depositing of the metal compounds can be carried out by means of cathode sputtering techniques, photolithography and wet and dry etching (by plasmas) or electrodeposition techniques. In a particular example, it was carried out by means of depositing and photolithography techniques, to that end, a layer of metal was deposited on the surface of SU-8 without microchannels by conventional sputtering or evaporation depositing techniques. A photoresin (5) with a thickness of 1 micron was then deposited on this layer, which photoresin was photolithographed defining the areas where the metal had been eliminated. This photoresin was developed and the exposed layers of metal were eliminated by means of chemical etching. This chemical etching depended on the metal or combinations of metals used. After this step, the photoresin was eliminated using acetone, methanol or the PGMA developer. It is important to emphasize that the chemical etchings used are compatible with SU-8. Once the metal lines had been defined, another layer of SU-8 was deposited on them with the same method explained in the previous paragraph. This layer was photodefined in the areas where the microchannels are to be placed, or wherein the metal contacts of the metal lines with the outer medium are to be made.

Figure 3:
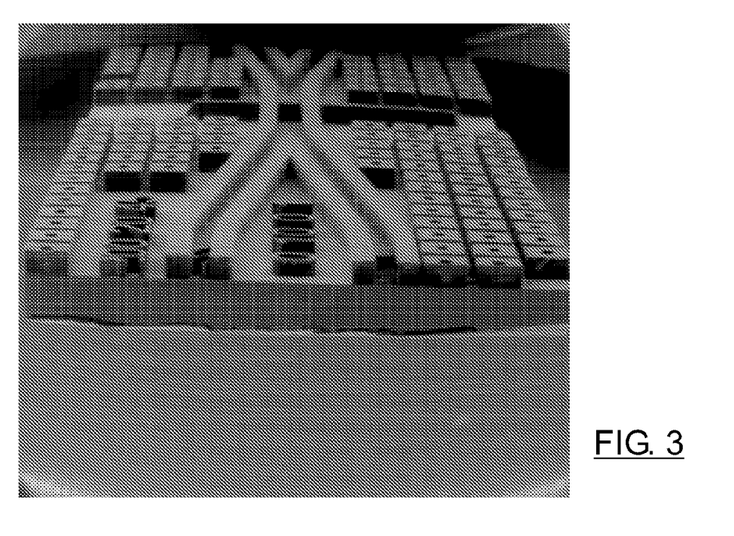
FIG. 3 shows a perspective view of the microfluidic microdevices with incorporated micromechanical structures
Figure 4:
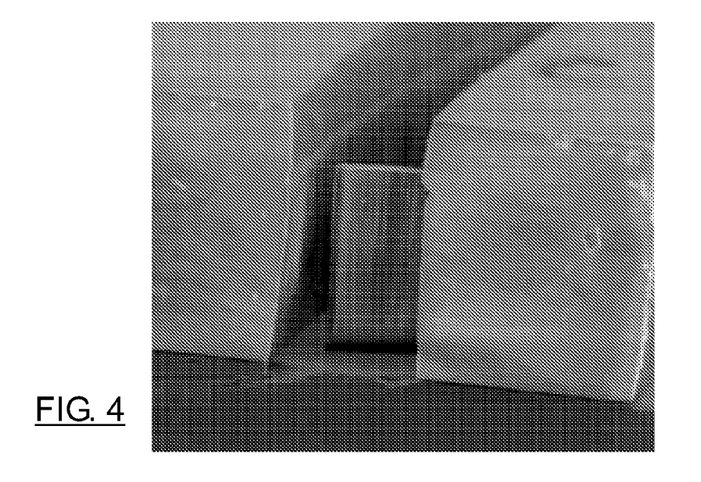
FIG. 4 shows a detail of the overhanging micromechanical structures FIG. 5 schematically shows an electrophoresis chip

Overhanging micromechanical structures were incorporated in one of the wafers (FIGS. 3 and 4). To that end, a layer between 3-5 µm of thick positive photoresin SPR 220-7.0 (Megaposit) was spread on a flat substrate using the following recipe for the spinning plate:

|        | time (s) | rpm  | acceleration |
|--------|----------|------|--------------|
| Step 1 | 10       | 200  | 100          |
| Step 2 | 5        | 600  | 200          |
| Step 3 | 60       | 6000 | 500          |
| Step 4 | 6        | 0    | 500          |
| Step 5 | 0        | 0    | 1000         |

If there are problems of adhesion to the substrate, the latter can be improved by previously applying Primer S1818 (Shipley) and using the previously described spinning recipe. The SPR 220-7.0 photoresin was then spread.

Once the layer of 4 µm had been deposited, the wafer was then heated in a 6° C./min gradient from 30° C. to 115° C. Once the maximum temperature of the gradient was reached, the wafer was left for 2 minutes and the temperature was then reduced in a natural gradient until it was lower than 80° C. The wafer was then exposed to UV rays for the purpose of defining the supports of the free structures. The total dose was 1 J/cm$^2$. The structures were developed by introducing the wafer in the MF-24A developer for 4 minutes and stirring slightly. The wafer was then rinsed in deionized water and dried.

To prevent the solvent of the structural SU8-50 photoresin from etching the SPR 220-7.0, the photoresin was subjected to a thermal treatment. To that end, the wafer was heated in a 60° C./min gradient to 150° C. Once the maximum temperature of the gradient had been reached, the wafer was left for 60 minutes and the temperature was then reduced in a natural gradient to room temperature.

The free structures were defined on the supports by spreading a layer of SU8-50 directly on them. The processing of SU8-50 was not altered by the method described.

The structures in SU8-50 were released during the developing process by simply introducing the wafer in PGMEA. SPR 220-7.0 dissolved in contact with said developer. The subsequent processing of SU8-50 was not altered by this method.

Figure 1:
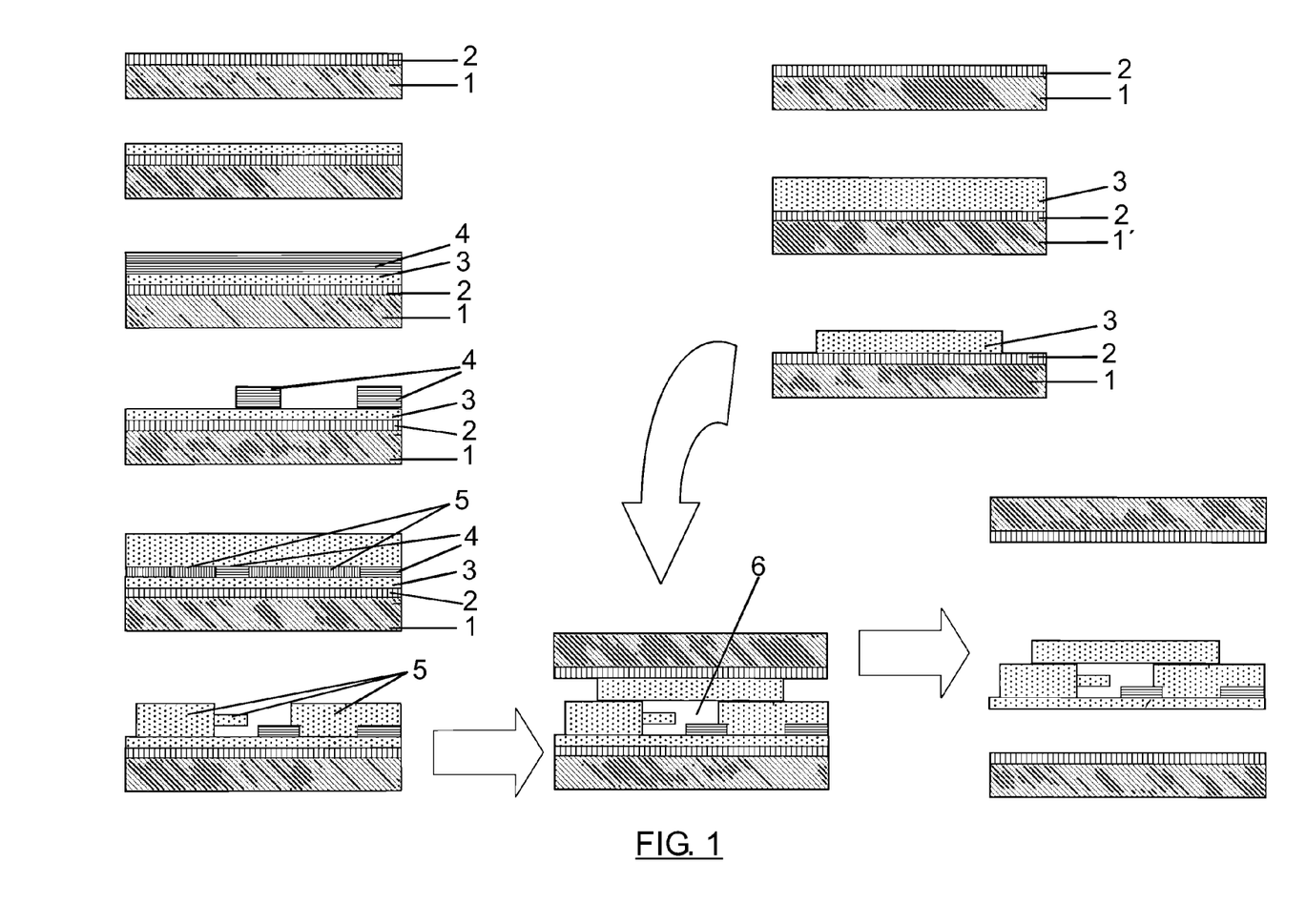
FIG. 1 shows a general diagram of the method for manufacturing the micro/nanofluidic devices

Once the channels 6 and the overhanging metal structures (4) were defined in both substrates, they were superimposed and bonded by means of a sealing process. The standard sealing process for sealing SU-8 resin with itself is traditionally carried out at a temperature of 100° C. (F J Blanco, M Agirregabiria, J Garcia, J Berganzo, M Tijero, M T Arroyo, J M Ruano, I Aramburu and Kepa Mayora. Novel three dimensional embedded SU-8 microchannels fabricated using a low temperature full wafer adhesive bonding. Journal of Micromechanics and Microengineering 14 (2004) 1047-1056). FIG. 1 shows the diagram of the manufacturing process. This process was carried out in a bonding tool for bonding by melting and pressure, a Suss SB6 Bonder (Suss Microtech, Germany). The wafers were first aligned in the Mask aligner (MA6) and then transferred to the bonding chamber separated by spacers. The bonding chamber was subsequently evacuated to $10^{-3}$ mbar. Before the contact, two heaters (in the bottom and in the upper part) uniformly heated the wafers at a temperature between 70 and 85° C. for 3 minutes, allowing the moisture to evaporate and preventing any empty formation. The wafers were then put in contact with one another and heating of the wafers began at a temperature from between 80 to 120° C., applying a pressure from between 100 and 500 KPa for 20 minutes.

Once the sealing process had finished, the devices were submerged in an IPA bath and subjected to ultrasound for 1 minute. This bath fulfills two functions, that of releasing the layers of Kapton, PEB or Mylar from the rigid substrates and cleaning the devices. Once the layers of Kapton, PEB or Mylar had been released from the substrates, they were manually removed from the devices of SU-8, without damaging the structures. The structures of the devices were freed in the entire substrate, and the devices could be cut manually in a simple manner.

Figure 2:
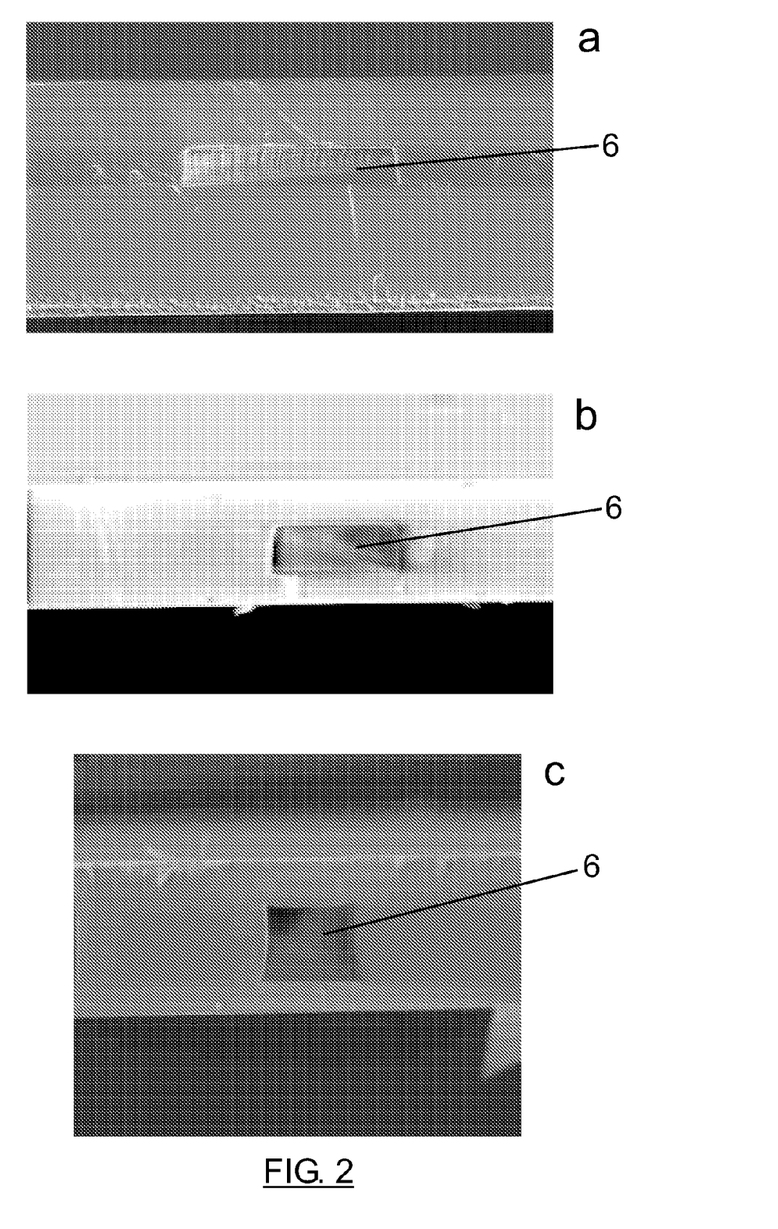
FIG. 2 shows details of microchannels with different dimensions a) 20×50 b) 60×50 c) 90×50

As a result, rectangular microchannels 6 (FIG. 2) with a high definition compared to other technologies for manufacturing microfluidic devices in polymers were obtained.

Example 1

Electrophoresis Chip

The manufacturing process described gave rise to an electrophoresis device for separating proteins. These biomolecules contain a net charge and upon applying an electric current in the microchannel in which they are located, they start to move with different speeds, according to their size and charge. They are thus separated. This technique is widely used in the proteomics field in several applications such as the diagnosis of diseases or the discovery of new drugs. This device allows carrying out these proteomic analyses quickly and accurately, reducing the costs of conventional systems.

Figure 5:
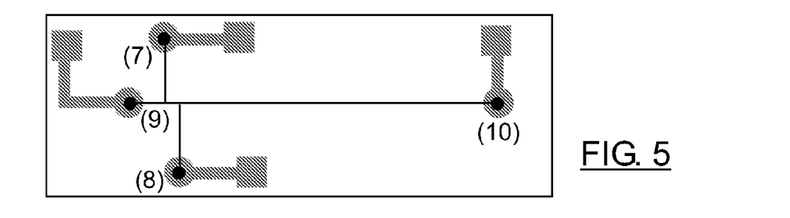

As seen in FIG. 5, the design of this device is based on two channels placed in a T shape and four platinum electrodes placed at each of the inlets (7 and 9) and outlets (8 and 10) of the channels. The vertical microchannel starting at inlet 7 and ending at outlet 8 is the channel which is used to electrokinetically inject the sample. The horizontal microchannel starting at inlet 9 and ending at outlet 10 is the channel where the sample is separated.

The manufacture of this device was based on the process described in the previous paragraphs. In a summarized manner, it can be stated that it consisted of sealing two substrates of Kapton in which the structures had been previously defined by photolithography. Firstly, a continuous layer of SU-8 of 20 microns was polymerized in the bottom substrate. The platinum electrodes were then manufactured by means of evaporation and chemical etching and, above these electrodes, the two channels in a T shape and the openings of the electrodes were defined by means of another SU-8 photolithography. In addition, the covers of these channels and the openings of the electrodes were manufactured in the top substrate, using the same photolithography process. Finally, the two substrates were sealed and the devices were released.

Figure 6:
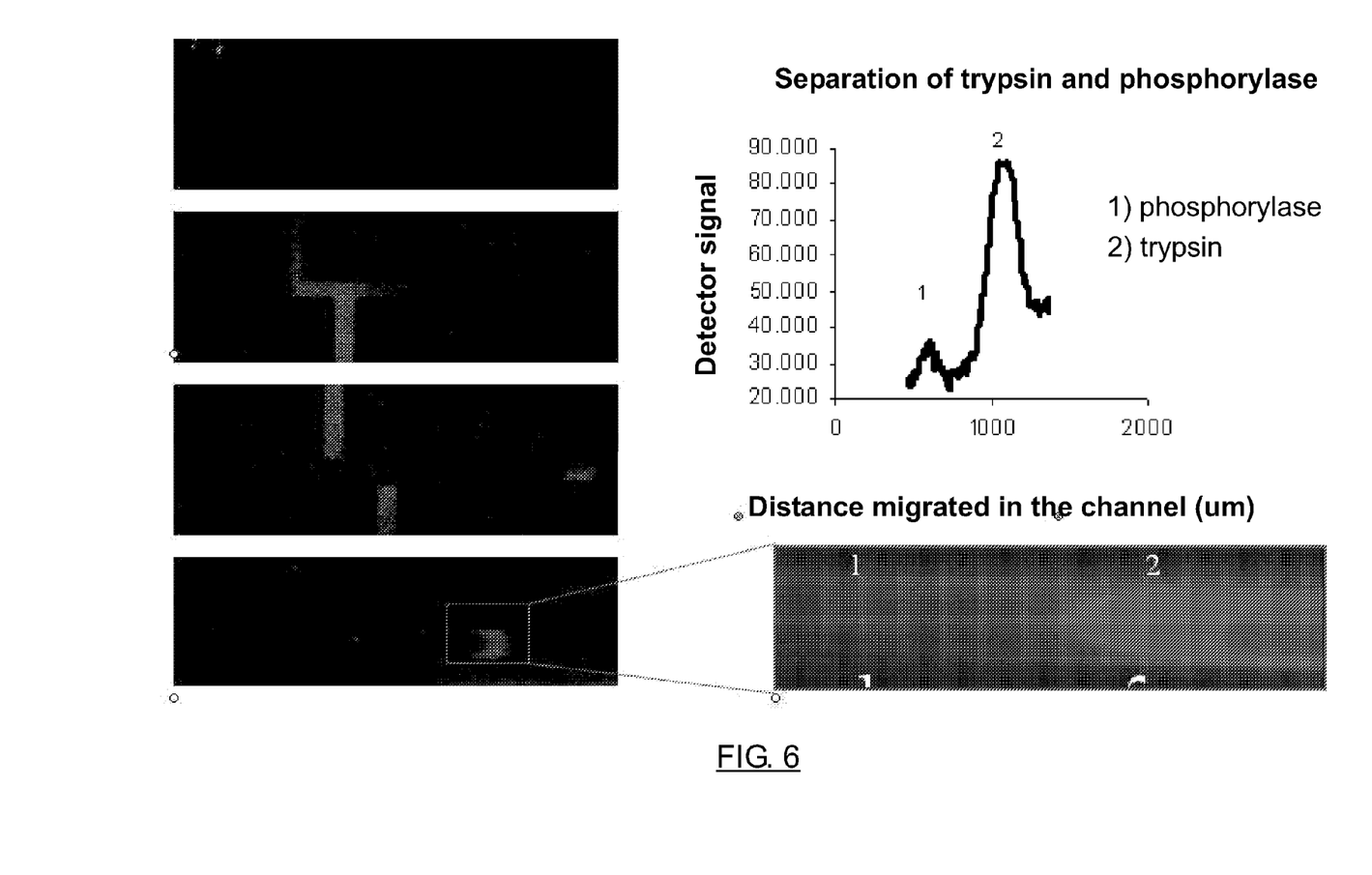
FIG. 6 shows the result of the injection and the separation of two proteins after applying voltage through the electrodes of the device

FIG. 6 shows the result of the injection and the separation of two proteins after applying voltage through the electrodes of the device.

Example 2

Microcannulas

Figure 7:
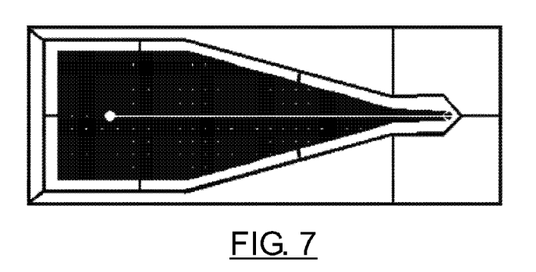
FIG. 7 shows the design of microcannulas.
Figure 8:
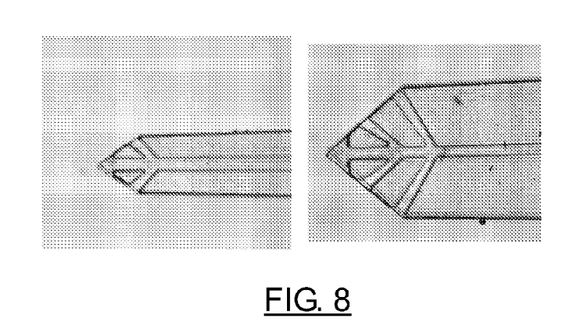
FIG. 8 shows in detail the microchannels in the microcannulas.
Figure 9:
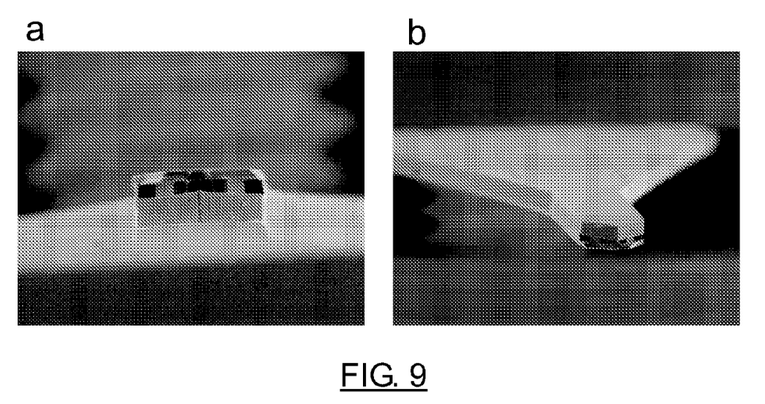
FIGS. 9a and 9b show electron microscope photographs of the microcannulas.

Due to the nature of the manufacturing processes, microcannulas with embedded microfluidic channels were designed which allowed directly introducing medicinal products into the damaged tissues or organs. These microcannulas have great advantages over those made with other technologies in silicon or in another type of polymer. Due to the manual cut, it is possible to make structures that are very complex and have a high-definition, which is only limited by the resolution of the photolithography process, which in a commercial aligner can reach hundreds of nanometers. FIG. 7 shows a design of a microcannula with the microfluidic channel which is closed with the sealing process. The structures securing the microcannula to the substrate have dimensions of 100 microns in width. These structures can be easily removed from the microcannula without any damage to the material. The manufactured insertion tips are shown in the electron microscope photographs, FIG. 9a and FIG. 9b. The outlets of the embedded microfluidic channels can be seen. Insertion tests in materials similar to the tissue of some organs of the human body, specifically with gelatins, have been carried out. The tips easily penetrate the gelatin, and allow delivering liquids therein Example 3

Implantable Microcannulas for Applications as
Medicinal Product Delivery Devices and Monitoring
the State of Tissues with Impedance Measurements These devices allow accurately delivering drugs inside damaged tissues, as well as monitoring different parameters therein.

The incorporation of sensor electrodes in these microfluidic devices involves a key advantage because said devices allow monitoring the state of the tissue during the drug delivery process. The manufacturing method allows the sensors to be placed at about 5-20 microns embedded inside the device, compared to the hundreds of microns in the processes of the state of the art. This makes the sensor electrodes be in better contact with the tissues on which the device is implanted. Furthermore, this manufacturing process allows obtaining individual devices without needing to use the cutting process, being able to achieve different shapes which cannot be achieved by means of the usual cutting processes used in the manufacture of microsystems (laser or disc cutter). This is another essential improvement when designing devices which can be adapted to the organ in which they will be implanted.

Figure 10:
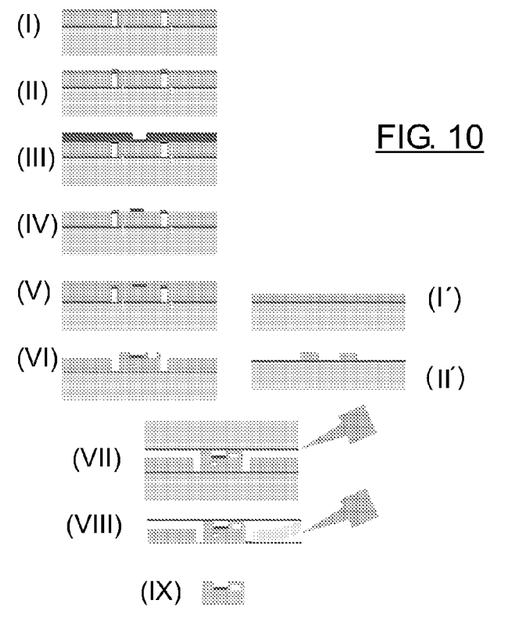
FIG. 10 shows the diagram of the manufacturing process in the particular case in which the device contains sensor electrodes.

FIG. 10 shows a diagram of the manufacturing process in the particular case that it contains sensor electrodes. The process starts by depositing a layer of SU-8 on a rigid substrate (glass or silicon) on which a sheet of Kapton has been adhered with a resin (S1818). This layer of SU-8 is photolithographed but not developed. This photolithography process defines the final shape of the devices. The innovation starts by depositing on the SU-8 two metal layers (I), a first layer of chromium (Cr, 50 nm) and on top of it a layer of gold (Au, 150 nm). Both layers are deposited by means of sputtering evaporation depositing techniques, and their function is to place a physical barrier between the non-polymerized SU-8 and the photoresin which will define the shape of the electrodes. During this sputtering evaporation depositing technique, it is possible to polymerize the non-polymerized SU-8 by temperature. This polymerization during the sputtering evaporation depositing causes an unwanted stress effect between the SU8 resin and the deposited metal. Said stress, due to the different coefficients of thermal expansion, is minimized by carrying out the sputtering evaporation depositing process at low temperature. Once this first metallization has been carried out, a photoresin (S1818) is deposited which will serve to structure the sheet of metal (Cr/Au). The photoresin is photostructured such that it only covers the non-polymerized areas of SU-8, and the rest of the metal is chemically etched, only that protected by the photoresin remaining (II). The electrode metallization process will be started on the polymerized and non-polymerized (protected by metal) structures, which electrodes are platinum (Pt)/titanium (Ti) electrodes in a special configuration. Firstly, a layer of photoresin (SPR) is deposited and photostructured, on which layer the electrodes are deposited by means of sputtering techniques (III). Like in the previous sputtering evaporation depositing, thermal stress problems are minimized by reducing the temperature of the process. The SPR photoresin is etched with methanol, leaving the metal electrodes already defined on the areas of polymerized SU-8 (IV). Another layer of SU-8 is defined on these structures, where microfluidic channels and the sensor areas where the electrodes must be in contact with the external medium are defined (V and VI). To seal these microfluidic channels, a layer of SU-8 is deposited on another transparent (glass) rigid substrate coated with Kapton (II'). Both wafers are aligned in a commercial contact aligning machine, and are introduced in wafer sealing equipment. By applying the same sealing conditions used in the previously described general process, the layers of SU-8 are melted maintaining the structure of the microchannels and of the electrodes without deformation. The wafers are removed from the Kapton in an ultrasound methanol bath, etching the photoresin which has been used to adhere the layer of Kapton to the rigid substrates (VII). Given the low adhesion of Kapton to SU-8, the structures can be easily removed manually from the substrate (VIII), freeing the semiflexible and metallized microdevices of SU-8 (IX).

Figure 11:
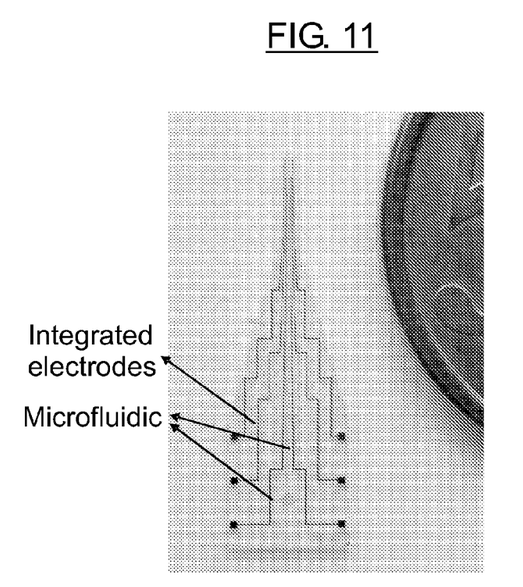
FIG. 11 shows a device in SU-8 integrating microfluidic channels for delivering drugs together with sensor electrodes.
Figure 12:
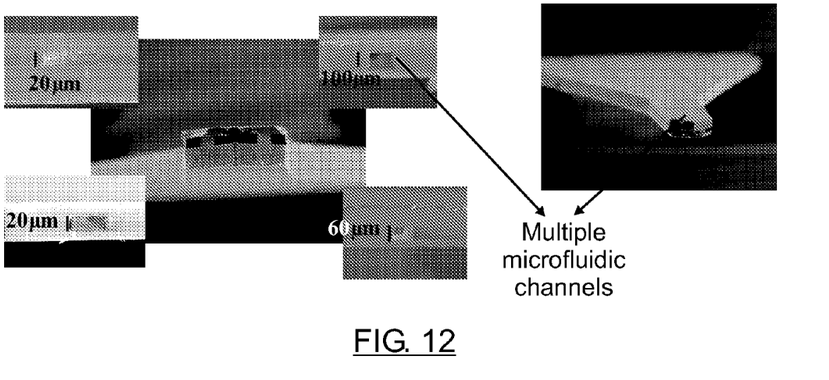
FIG. 12 shows electron microscope (SEM) photographs of different structures of microfluidic devices.

FIG. 11 shows a typical structure obtained by means of this manufacturing process. FIG. 12 shows photographs obtained of different devices with an electron microscope (SEM).

During the first tests on animals, a poor adherence of the metal layers to the SU-8 polymer was observed. Metal layers generally have greater problems of adhesion on plastics than on silicon or glass (the materials which have been used up until now in manufacturing these devices). This adherence has been improved using oxygen plasma cleaning processes for the surfaces of SU8 combined with different doses of exposure of the polymer. The quality of the adhesion has passed different tests according to the corresponding ASTM (AMERICAN SECTION OF INTERNATIONAL ASSOCIATION FOR TESTING MATERIALS) standard.

Figure 13:
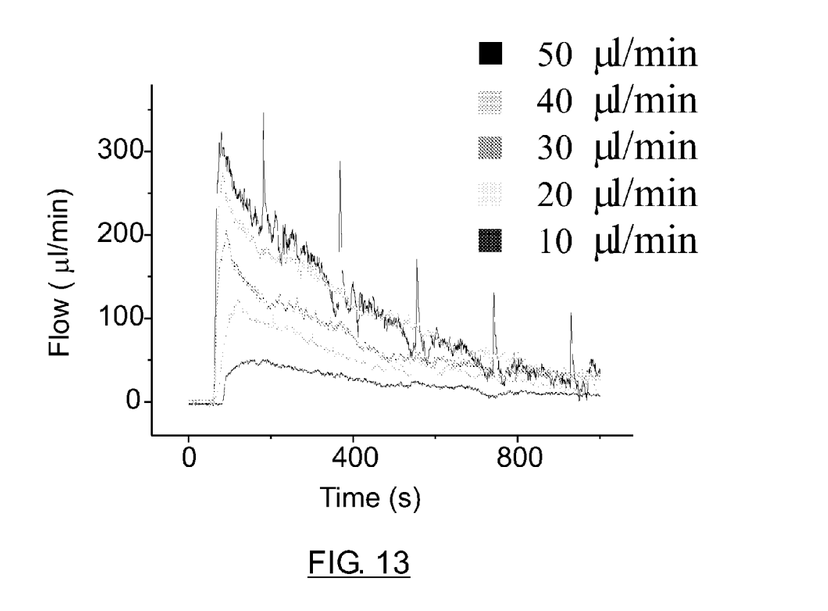
FIG. 13 shows a graph of the flow measured during the injection of deionized water into the gel at constant pressure.

Tests for using these devices as drug delivery devices in (brain) tissues have been carried out. To that end, a gel with porosity and mechanical properties similar to brain tissue has been synthesized. The gel used is agarose gel at a concentration of 0.6% by its weight/volume ratio. FIG. 13 shows the delivery flow measurements inside the gel. Flows between 10-50 microliters/minute, in channels of 40 microns in height and 50 microns in width, can be seen. These flows correspond to liquid injection pressures in the microdevice from between 0.1 to 1 bar. The peaks observed in the delivery at 50 microliters per minute correspond to a backflow of the delivered liquid. This is one of the serious problems found in the clinical tests of fluidic devices delivering drugs in the body. These results improve the results obtained with standard fluidic devices (cannulas) as well as those manufactured in silicon, which have backflow problems at much lower flows. Backflow problems have been minimized with these new microdevices and this is another advantage of using these microdevices in drug delivery applications.

The invention claimed is:

1. A method for manufacturing micro/nano-fluidic devices comprising:
   a) depositing a thermosetting polymeric photo-resin on two substrates of biocompatible polymeric material, each of the substrates of biocompatible polymeric material covering the surface of one of two independent wafers, comprising a first wafer and a second wafer;
   b) performing a photolithography step at low temperature on the layers of thermosetting polymeric photo-resin deposited in step a);
   c) depositing metal type components on at least one wafer covered by the one of the substrates of biocompatible polymeric material and the polymeric photo-resin deposited in step a);
   d) microstructuring the metal-type components deposited in step c);
   e) depositing a layer of thermosetting polymeric photo-resin on the second wafer;
   f) performing a photolithography step at low temperature on the thermosetting polymeric photo-resin deposited on the second wafer;
   g) sealing at low temperature the first and second wafers obtained by superimposing the first and second wafers with the surfaces of the photo-resin facing one another;
   h) releasing the micro/nano-fluidic devices from the substrates of biocompatible polymeric material;
   i) cutting the micro/nano-fluidic devices.

2. The method for manufacturing micro/nano-fluidic devices according to claim 1, wherein the polymeric photo-resin deposited in step e) is an epoxy resin.

3. The method for manufacturing micro/nano-fluidic devices according to claim 1, wherein the polymeric photo-resin deposited in step e) is SU-8.

4. The method for manufacturing micro/nano-fluidic devices according to claim 1, wherein step a) is repeated at least once.

5. The method for manufacturing micro/nano-fluidic devices according to claim 1, wherein the step of photolithography at low temperature of step b) is carried out at temperatures comprised between 80-95° C.

6. The method for manufacturing micro/nano-fluidic devices according to claim 1, wherein there is a step prior to step g) wherein overhanging micromechanical structures are made.

7. The method for manufacturing micro/nano-fluidic devices according to claim 1, wherein the sealing of step g) is carried out at temperatures comprised between 80° and 120° C.

8. The method for manufacturing micro/nano-fluidic devices according to claim 1, wherein the sealing of step g) is carried out at pressures comprised between 100 and 500 KPa.

9. The method for manufacturing micro/nano-fluidic devices according to claim 1, wherein the micro/nanofluidic structures of step h) are released by means of ultrasound in an alcohol bath.

10. The method for manufacturing micro/nano-fluidic devices according to claim 1, wherein the cutting of step i) is a manual cutting step.

11. The method for manufacturing micro/nano-fluidic devices according to claim 1, wherein the micro/nanofluidic devices are microcannulas, microprobes, electrophoresis chips, electrospray chips.

12. A micro/nano-fluidic device obtained by the method according to claim 1, further comprising forming at least one micro/nanofluidic channel, wherein the channels and thickness dimensions of the micro/nano-fluidic device are comprised between 500 microns and 500 nanometers.

13. The micro/nano-fluidic device according to claim 12, wherein the micro/nanofluidic channels comprise dimensions between 5 and 500 microns in width and between 1 and 500 microns in height.

14. The micro/nano-fluidic device according to claim 13, wherein the micro/nanofluidic channels comprise dimensions between 10 microns and 200 microns in height.

15. The micro/nano-fluidic device according to claim 12, comprising microchambers with width dimensions comprised between 1 and 5 mm and height dimensions comprised between 20 and 180 microns.

16. A method of using a device according to claim 12, the method being selected from the group consisting of clinical diagnosis, medicinal product delivery, monitoring of the state of tissues, fluid extraction, neural prostheses, electrophoresis chips, microcannulas, and microprobes.

* * * * *